United States Patent
Vogt

(10) Patent No.: US 9,964,100 B2
(45) Date of Patent: May 8, 2018

(54) COMPRESSED GAS MOTOR FOR OPERATION OF A LAVAGE SYSTEM

(71) Applicant: Heraeus Medical GmbH, Wehrheim (DE)

(72) Inventor: Sebastian Vogt, Erfurt (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 347 days.

(21) Appl. No.: 14/681,183

(22) Filed: Apr. 8, 2015

(65) Prior Publication Data
US 2015/0308421 A1 Oct. 29, 2015

(30) Foreign Application Priority Data
Apr. 29, 2014 (DE) .................. 10 2014 208 064

(51) Int. Cl.
  *F04B 9/12* (2006.01)
  *A61M 3/02* (2006.01)
  *F04B 7/02* (2006.01)
(52) U.S. Cl.
  CPC .............. *F04B 9/12* (2013.01); *A61M 3/0254* (2013.01); *A61M 3/0258* (2013.01); *F04B 7/02* (2013.01)
(58) Field of Classification Search
  CPC ........... F04B 9/12; F04B 7/02; A61M 3/0258; A61M 3/0254
  See application file for complete search history.

(56) References Cited

U.S. PATENT DOCUMENTS

| 2,944,521 A | 7/1960 | Kibbe, Jr. |
| 3,937,055 A | 2/1976 | Caruso et al. |
| 4,278,078 A | 7/1981 | Smith |
| 4,583,531 A | 4/1986 | Mattchen |
| 4,700,611 A | 10/1987 | Kaneko |
| 5,520,667 A * | 5/1996 | Roche .................. A61F 2/4675 604/290 |
| 5,542,918 A | 8/1996 | Atkinson |
| 2013/0180396 A1 | 7/2013 | Vogt et al. |

FOREIGN PATENT DOCUMENTS

| DE | 34 34 033 A1 | 4/1985 |
| DE | 10 2010 046 057 B3 | 1/2012 |
| DE | 10 2011 018 708 A1 | 10/2012 |

(Continued)

OTHER PUBLICATIONS

Office Action for corresponding Japanese Patent Application No. 2015-085743, dated Aug. 30, 2016.

(Continued)

*Primary Examiner* — Andrew Gilbert
*Assistant Examiner* — Hamza Darb
(74) *Attorney, Agent, or Firm* — Norris McLaughlin & Marcus P.A.

(57) ABSTRACT

A compressed gas motor (1) comprising a vibration body (10) made to vibrate by a compressed gas being guided through the compressed gas motor (1), and a plunger (12) supported as in a bearing by a restoring element (14) in spring-like manner, the vibration body (10) and the plunger (12) being positioned and supported such that the vibration body (10) repeatedly hits against the plunger (12) during the vibration and displaces it against the restoring element (14), whereby the motion of the plunger (12) is utilized as the drive of the compressed gas motor (1).

26 Claims, 6 Drawing Sheets

(56) References Cited

FOREIGN PATENT DOCUMENTS

| | | |
|---|---|---|
| GB | 2 114 495 A | 8/1983 |
| JP | 1990-230977 A | 9/1990 |
| JP | 1996-334082 A | 12/1996 |
| WO | 2012/038003 A1 | 3/2012 |

OTHER PUBLICATIONS

Australian Examination Report dated Oct. 7, 2015.
Breusch et. al., "Lavage Technique in Total Hip Arthroplasty". J. Arthroplasty, 2000, vol. 15, No. 7, pp. 921-927.
Breusch et. al., "Zementierte Hüftendoprothetik, Verminderung des Fettembolierisikos . . . ", Orthopädie 2000, No. 29, pp. 578-586.
Byrick et al., High-Volume, High Pressure Pulsatile Lavage during Cemented Arthroplasty, J. Bone and Joint Surgery, 1999, vol. 71-A, No. 9, pp. 1331-1336.
Christie et al., "Medullary Lavage Reduces Embolic Phenomena and Cardiopulmonary . . . ", J. Bone and Joint Surgery, 1995, vol. 77-B, No. 3, p. 456-459.
Sherman et. al. The Role of Lavage in Preventing Hemodynamic . . . , J. Bone and Joint Surgery, 1983, vol. 65-A, No. 4, p. 500-501.
Office Action by the German Patent Office dated Jan. 23, 2015 in the corresponding application.
Canadian Office Action dated Jan. 20, 2016.

\* cited by examiner

COMPRESSED GAS MOTOR FOR OPERATION OF A LAVAGE SYSTEM

The invention relates to a compressed gas motor comprising a plunger and a restoring element. The invention also relates to a lavage system comprising a compressed gas motor of this type.

Moreover, the invention relates to the use of a compressed gas motor of said type and to a method for generating a periodical motion by means of a compressed gas, and to a method for generating a spray puff by means of a method of said type.

Accordingly, the object of the invention is a simplified compressed gas motor that can be manufactured, in part, from inexpensive plastic materials and is well-suited as a pumping drive of medical rinsing devices. Moreover, a pump for liquids that is driven by the compressed gas motor is described. Moreover, the invention proposes the use of the compressed gas motor to drive a pump for dispensing rinsing liquid for a medical rinsing device (i.e. for a lavage system). But the compressed gas motor can be used for other purposes just as well.

BACKGROUND OF THE INVENTION

Medical rinsing systems are used widely in surgery to clean tissue areas. Said rinsing systems are called lavage systems. The lavage systems and rinsing liquids are used to produce spray jets that impinge on the tissue areas to be cleaned and exert a mechanical cleaning effect on said tissue areas. Specifically during the implantation of articular endoprostheses and during septic revisions, lavage systems have essential significance (R. M. Sherman et al.: The role of lavage in preventing hemodynamic and blood-gas changes during cemented arthroplasty. J. Bone Joint. Surg. 1983; 65-A: 500-506; S. J. Breusch et al.: Zementierte Hüftendoprothetik: Verminderung des Fettembolierisikos in der zementierten Hüftendoprothetik mittels gepulster Druckspülung. Orthopädie 2000; 29: 578-586; S. J. Breusch et al.: Lavage technique in THA: Jet-lavage Produces Better Cement Penetration Than Syringe-Lavage in the Proximal Femur. J. Arthroplasty. 200; 15(7): 921-927; R. J. Byrick et al.: High-volume, high pressure pulsatile lavage during cemented arthroplasty. J. Bone Joint Surg. 1989; 81-A: 1331-1336; J. Christie et al.: Medullary lavage reduces embolic phenomena and cardiopulmonary changes during cemented hemiarthroplasty. J. Bone Joint Surg. 1995; 77-B: 456-459).

Pulsed lavage systems have been known for a long time, for example from U.S. Pat. No. 4,583,531 A, U.S. Pat. No. 4,278,078 A, and U.S. Pat. No. 5,542,918 A. The lavage systems currently on the market are driven by means of electrical motors (for example InterPulse® Jet lavage made by Stryker GmbH & Co. KG) or compressed air (for example PALAVAGE® made by Heraeus Medical GmbH). Hand-held, electrically-driven lavage systems have also proven useful. However, a large battery block or rechargeable battery block, which only has a limited charge capacity due to its nature, always needs to be taken along. Battery blocks and rechargeable battery blocks are viewed critically in terms of their environmental impact. Compressed gas-driven lavage systems are advantageous in that compressed air is usually available in the operating theatre in unlimited quantities and thus allows rinsing liquid to be sprayed for any desired time without the energy supply being limited.

However, using compressed air-driven lavage systems requires the use of a two-tube system, in which the non-sterile compressed air is supplied through one tube and a second tube is used to discharge the non-sterile air, which is partially expanded after it drives the compressed air motor. However, systems driven by compressed air or any other compressed gas usually utilise a compressed gas motor as the drive. Most compressed gas motors for lavage systems are lamellar compressed gas motors. The compressed gas motor generates a rotary motion which is then translated into an oscillating linear motion. The oscillating linear motion is utilised to convey momentum to small volumes of the rinsing medium. It is common in this context to arrange at least one membrane between the drive and the inlet of rinsing liquid in order to be able to transmit the pulses to the rinsing liquid. This generates spray puffs at high pulse rates of 2,000 to 3,000 pulses per minute. This means that the compressed gas motor needs to be manufactured at high precision in order to tolerate such high rotation rates. Moreover, sufficiently stable storage must be available. For these reasons, the compressed gas motor is the most expensive component of common compressed air-driven lavage systems. Therefore, the compressed gas motor is generally arranged in a handle made of metal or other durable materials such that this component can be used multiply after appropriate reprocessing and sterilisation. Compressed gas motors utilise the pressure difference between the compressed gas used to drive the motor and the pressure of the ambient atmosphere. Theoretically, they could also be operated by means of a negative pressure applied to the gas outlet, since it is just the pressure difference that is important in this context.

A compressed gas motor is known from DE 10 2010 046 057 B3, in which a plunger system generates a periodical motion that can also be used to pump liquids.

A proposal related to the generation of pulsed liquid jets is described in DE 10 2011 018 708 A1. In this context, a plunger vibrator acts periodically on a membrane. The membrane and a hollow space jointly form a pump.

However, one disadvantage of all pumps with a membrane is that it is very difficult to manufacture a suitable membrane with a high restoring force that can follow the high pulse rates of a plunger vibrator and/or vibration body. As a result, high pulse rates can be implemented only with great effort. Moreover, said systems are sensitive due to the axial deformability of the membrane, since the vibration body can move too far axially into the direction of the membrane and thus might come to a standstill. Said systems are not sufficiently robust.

Other compressed gas motors can get locked by the plungers lodging and thus locking. Moreover, the plungers might take on a position, in which the compressed gas motor does not restart by itself without further ado.

Compressed gas motors are well-suited not only for lavage systems, but can also be used in all applications, in which a compressed gas is available and an inexpensive drive is advantageous. Said requirements are evident, for example, in shaker facilities, in which bulk goods or powder need(s) to be transported, filled into containers and/or dosed. Likewise, said compressed gas motors can be used to advantage as pumps providing lubricants.

Accordingly, it is the object of the invention to overcome the disadvantages of the prior art. Specifically, the object is to discover an inexpensive and reliable compressed gas motor that can be used for the afore-mentioned purposes. The invention is therefore based on the object to develop a robust, maximally simplified medical rinsing device that can generate a pulsed liquid jet, whereby the pulse rate shall exceed, in particular, 1,000 pulses per minute. It shall be feasible to manufacture the device largely from inexpensive materials and to drive the device by compressed gas. The medical rinsing device to be developed can be intended for single use. The rinsing device shall be well-suited for operation with compressed air from stationary compressed air supply systems and for operation with compressed gases from mobile compressed gas bottles or gas cartridges.

It is an object of the invention to develop a maximally simplified plunger-equipped compressed gas motor that can generate a periodical linear plunger motion. It shall be feasible to operate the compressed gas motor with the compressed gas from stationary compressed gas facilities that are common in hospitals. Moreover, a method for generating a linear periodical motion is to be developed, in which the compressed gas motor to be developed is to be used or at least is usable. It is important in this context that the compressed gas motor works without complex costly valve systems and is simplified to the extent that as many components of the compressed gas motor as possible can be produced inexpensively through injection moulding of plastic materials or by turning of easily processing metal bodies. The compressed gas motor shall be usable to drive a medical rinsing device. Valve systems that take up a large volume and need to be positioned separately from the compressed gas motor need to be avoided. Accordingly, the requisite valve functions shall be integrated into the compressed gas motor in space-saving manner in order to enable the use of the compressed gas motor as a drive in hand-pieces of lavage systems. Ideally, the time control of the valve functions should be implemented appropriately such that there is no "dead centre" at any point of the plunger motion. Moreover, a simplified pump for integration into hand-held lavage systems is to be developed along with the compressed gas motor. A pump driven by the compressed gas motor shall be simplified to the extent that it can be manufactured inexpensively enough to also allow it to be used in lavage systems intended for single use only.

SUMMARY OF THE INVENTION

The objects of the invention are met by a compressed gas motor comprising a vibration body that can be made to vibrate by a compressed gas being guided through the compressed gas motor, and a plunger that is supported as in a bearing by a restoring element in spring-like manner, whereby the vibration body and the plunger are appropriately positioned and supported as in a bearing such that the vibration body repeatedly hits against the plunger during the vibration and displaces it against the restoring element, whereby the plunger can be transferred by the restoring element into a position, in which the vibration body hits against the plunger during its vibration, such that the vibration body repeatedly hits against the plunger during the vibration, and whereby the motion of the plunger can be utilised as the drive of the compressed gas motor.

DETAILED DESCRIPTION

In the scope of the present invention, a compressed gas motor shall be understood to be a motor that can perform work by means of a pressure difference between a first gas (the compressed gas) and a second gas (for example of the surroundings) having a lower pressure. It is preferred in this context to use a compressed gas as working medium and to discharge it into the surroundings of the compressed gas motor. The flow of the compressed gas through the compressed gas motor makes the vibration body and thus the plunger perform a periodical motion.

Compressed gas motors according to the invention can be provided appropriately such that the restoring element exerts on the plunger a force acting in the direction of the vibration body, at least for part of the time during the operation of the compressed gas motor.

Preferably, the restoring element exerts a force in the direction of the vibration body while the plunger is in any position other than the starting position or the resting position of the plunger.

This ensures that the vibration body can repeatedly hit against the plunger during the vibration and induce the plunger, as a result, to perform a vibration that can be utilised as the drive for the compressed gas motor.

The invention also proposes the compressed gas motor to comprise an internal space, whereby the vibration body and the plunger are arranged in the internal space such as to be mobile in linear direction and that the internal space is bordered by a front side, a closed rear side, and a circumferential side wall, whereby the plunger is arranged between the front side and the vibration body.

The cross-sectional surfaces of the two regions of the internal space are oriented perpendicular to the linear direction of motion of the vibration body and preferably also perpendicular to the linear direction of motion of the plunger.

According to a preferred embodiment, the invention can provide the front region and the rear region of the internal space to have cylindrical geometry with a circular base surface. In this context, the two regions of the internal space are prefered to be geometrically connected to each other by means of their base surfaces. Preferably, the cylinder axes of the cylindrically symmetric regions of the internal space are situated on the same axis. For this purpose, the plunger has a cylindrical symmetry with a circular base surface, whereby the radius of the plunger is selected to be equal in size to or somewhat smaller than the diameter of the front region of the internal space, and/or the radius of the plunger is selected to match the internal radius of the internal space. It is preferred according to the invention to have the vibration body be assembled from two cylindrical bodies with a circular base surface and different radii. In this context, the radii are selected appropriately such that the two cylindrical parts (bodies) of the vibration body fit into the front region and the rear region of the internal space. The plunger and the vibration body shall be mobile in the internal space, but also seal the internal space by means of their outer circumferences.

An internal space of this type largely closes the compressed gas motor with respect to the outside. This is advantageous for the operational safety, but also offers a number of options for the use of the compressed gas as a drive. For example, a gas suspension can be utilised to generate the periodical motion of the vibration body and the vibration body can be utilised in the way of a plunger by the compressed gas expanding in the internal space.

Compressed gas motors according to the invention can be provided appropriately such that the internal space comprises a front region having a small cross-sectional surface and a rear region having a large cross-sectional surface that is larger than the small cross-sectional surface, whereby the plunger is arranged in the front region of the internal space between the front side and the vibration body such as to be mobile in linear direction.

As a result, a forceful motion of the vibration body can be attained such that the plunger can be driven by a large momentum.

In this context, the invention can again provide the vibration body to comprise a front part having a small cross-section matching the small cross-sectional surface of the front region of the internal space such that the front part of the vibration body closes the front region of the internal space on the side facing the rear side at least for part of the time during the operation of the compressed gas motor, and provide the vibration body to comprise a rear part having a large cross-section matching the large cross-sectional surface of the rear region of the internal space such that the rear part of the vibration body separates the rear region of the internal space into two parts.

As a result, this attains a gas suspension for the vibration body that acts in a direction opposite to the plunger. If the front part of the vibration body closes the front region of the internal space on the side facing the rear side only for part of the time during the operation of the compressed gas motor, i.e. if it is open at times, or if fresh gas is supplied into said gap by other means during the motion of the vibration body, it can be ensured that a sufficient gas pressure for suspension of the vibration body is present at all times.

Moreover, the invention proposes to provide a gas inlet opening for supplying a gas into the internal space in the side wall in the rear region of the internal space and to provide a gas outlet opening for discharge of the gas from the internal space in the side wall in the front region of the internal space.

The invention can provide that the gas inlet opening can be connected to a compressed gas source. In this case, the compressed gas motor can be operated by means of a compressed gas from a compressor or a compressed gas bottle or a liquid gas cartridge, such as, for example, a $CO_2$ cartridge. The discharged air exiting from the compressed gas motor through the gas outlet opening can then be discharged to the surroundings.

This ensures that the compressed gas is guided past or through the vibration body and can thus be utilised to drive the vibration body.

A preferred refinement of the present invention proposes the internal space between the plunger and the rear side of the internal space to be closed except for the gas inlet opening and the gas outlet opening.

This prevents the compressed gas motor from loosing power due to escaping compressed air.

A refinement of the present invention proposes at least one channel guiding gas to be provided in the vibration body, whereby the channel or channels connects or connect the rear region of the rear internal space between the vibration body and the rear side of the internal space to the gas inlet opening or to the gas outlet opening depending on the position of the vibration body in the internal space.

As a result, a compact and failure-insensitive design of the compressed gas motor is attained. The channel or channels are designed to be gas-permeable for this purpose.

A particularly preferred embodiment of the present invention can provide the vibration body, in a first position, to connect the rear region of the internal space between the vibration body and the rear side of the internal space by means of the at least one channel to the gas inlet opening and to separate it from the gas outlet opening, and, in a second position, to connect the rear region of the internal space between the vibration body and the rear side of the internal space by means of the at least one channel to the gas outlet opening and to separate it from the gas inlet opening.

This design ensures that there is no short-circuit position, in which the gas inlet opening is connected to the gas outlet opening by means of the at least one channel and in which the compressed gas motor thus comes to a standstill. Moreover, it could not be started again in said position of the vibration body.

Moreover, the invention can provide the vibration body, in a third position between the first position and the second position, to cover both the gas inlet opening and the gas outlet opening.

As before, the purpose of this measure is to ensure that the compressed gas motor runs reliably and without stoppage.

For implementation of the invention, it is proposed to have the at least one gas-permeable channel extend from the side of the vibration body facing the rear side to the lateral jacket surface of the rear part of the vibration body and have the same or any other gas-permeable channel extend from the side of the vibration body facing the rear side to the lateral jacket surface of the front part of the vibration body. Preferably, the vibration body comprises just one gas-permeable channel that is designed as a tee and extends from the side of the vibration body facing the rear side to the lateral jacket surface of the rear part of the vibration body and to the lateral jacket surface of the front part of the vibration body.

As a result, a particularly simple and easily implemented design of the compressed gas motor is attained.

A refinement of the invention can just as well provide a liquid inlet opening in the front region of the internal space in the side wall of the internal space and provide a gas outlet opening in the front side of the internal space, whereby it is preferred to arrange a valve, preferably a lip valve, on at least one of the liquid openings, particularly preferably on both liquid openings.

In this context, the invention can provide the liquid inlet opening to be connected to a liquid supply and/or a source of liquid. The liquid is preferred to be a medical rinsing liquid.

Said embodiments can just as well provide a valve to be arranged on the liquid inlet opening and to open when a low pressure arises in the front region of the internal space due to a motion of the plunger away from the front side, and a valve to be arranged on the liquid ejection opening that opens when a high pressure arises in the front region of the internal space due to a motion of the plunger towards the front side.

As a result of said measures, the compressed gas motor can be used, directly and easily, as a pump and as a medical rinsing system, in particular as a lavage system.

According to a refinement of the present invention, it is proposed to have the liquid inlet opening, in operation of the compressed gas motor, not be covered by the plunger at least for part of the time, and have the liquid inlet opening, in the non-covered state, be arranged between the plunger and the front side of the internal space.

This ensures a good pumping effect.

Moreover, the invention can provide a tube or a hose with a non-return valve to be connected to the liquid inlet opening and to have the non-return valve open when there is a negative pressure in the front region of the internal space between the plunger and the front side of the internal space and to thus enable a supply of liquid into the front region of the internal space.

What this attains is that no liquid can be pushed from the compressed gas motor into the liquid reservoir. This is important, specifically, when the compressed gas motor is used to spray sterile medical liquids.

Moreover, the invention can provide the restoring element to be an elastic compression spring that is arranged, preferably, in the front region of the internal space between the plunger and the front side of the internal space.

This design is particularly easy and inexpensive to implement.

Preferred embodiments can be characterised in that the internal space, at least regions thereof, is cylindrical or is cylindrical in the region of a working space of the vibration body and/or of the plunger or in the entire swept volume of the plunger and vibration body.

As a result of said design, the compressed gas motor is particularly easy and inexpensive to build. Avoiding edges and corners can prevent the compressed gas motor from getting locked. Moreover, cylindrical shapes are particularly easy and inexpensive to manufacture.

The invention proposes the vibration body to have a higher density than the plunger.

It can be essential for compressed gas motors according to the invention that the vibration body has a density of at least 4 $g/cm^3$, preferably a density of at least 7 $g/cm^3$.

Said refinement, which is particularly essential according to the invention, ensures that the vibration body attains a sufficiently high kinetic energy and/or a sufficiently high momentum to hit and/or accelerate the plunger in the direction of the front side of the internal space with the requisite momentum and/or kinetic energy. The energy and/or the momentum must be sufficient to overcome the spring force of the compression spring and/or the elastic force of the restoring element to the extent that same becomes largely compressed and/or deflected.

For this purpose, the vibration body preferably is designed to be made of a metal or a high-density plastic material, preferably of brass, steel or any other easily processed metal or a plastic material filled with heavy spar or tungsten. According to the invention, the remaining compressed gas motor, with the exception of the restoring element, can be fabricated from a plastic material, such as polyethylene, and can be manufactured, for example, through an injection moulding method.

Moreover, the invention can provide the restoring element to move the plunger into a position, in which the front side of the front part of the vibration body, at maximal deflection of the vibration body in the direction of the front side of the internal space, hits against the side of the plunger facing the rear side of the internal space to accelerate same in the direction of the front side of the internal space.

According to the invention, it can be preferred in this context that the vibration body shifts the plunger by maximally 3 mm, particularly preferably by 1 mm to 3 mm, in the direction of the front side of the internal space.

The positions that can be assumed by the plunger and the vibration body in operation of the compressed gas motor, therefore overlap slightly, preferably by maximally 3 mm, particularly preferably by 1 mm to 3 mm, in the direction of motion of the vibration body. This is to ensure that the vibration body can transfer its momentum to the plunger.

A refinement of the invention proposes that the front part of the vibration body separates the front region of the internal space from the rear region of the internal space when the front part of the vibration body is arranged in the front region of the internal space.

This generates a gas suspension of the vibration body with respect to the part of the rear internal space facing the front side of the internal space by means which forms a border for the base surface of the rear part of the vibration body facing the front side of the internal space on the rear side. Said gas suspension drives the vibration body in the direction of the rear side of the internal space and thus back into its starting position.

In this context, the invention can preferably provide the vibration body to be appropriately shaped and appropriately supported as in a bearing in the internal space such that the front part of the vibration body is arranged in the front region of the internal space in any position of the vibration body. As a result, the front region of the internal space between the plunger and the vibration body is always separated from the gas suspension, i.e. is separated from the part of the rear internal space that faces the front side of the internal space and is bordered on the rear side by the base surface of the rear part of the vibration body facing the front side of the internal space.

According to another embodiment, the invention can just as well provide the plunger to touch against the internal wall of the front region of the internal space by its entire circumference, preferably to touch against the internal wall of the front region of the internal space by its entire circumference, in gas-tight-manner, and in pressure-tight manner and/or provide the vibration body to touch against the internal wall of the rear region of the internal space by its entire circumference, preferably to touch against the internal wall of the rear region of the internal space by its entire circumference, in gas-tight-manner, and in pressure-tight manner.

As a result, a compressed gas motor with a high degree of efficiency can be attained since the compressed air, all of it if possible, can be utilised to drive the vibration body and thus to perform the work.

It is preferred according to the invention not to use any rubber-elastic sealing rings in this context. Avoiding rubber-elastic seals is advantageous in that less friction is generated in the compressed gas motor and thus the compressed gas motor can run significantly faster and/or at a higher frequency.

The invention can just as well provide the vibration body to touch against the internal wall of the front region of the internal space by its entire circumference, preferably to touch against the internal wall of the front region of the internal space by its entire circumference, in gas-tight, and in pressure-tight manner. As a result, the rear part of the internal space can be separated from the front part of the internal space.

The invention can provide a circumferential wiper lip on the outer circumference of the plunger to seal the internal space. Preferably, said wiper lip is arranged on the side of the plunger facing the front side of the internal space.

Compressed gas motors running particularly stably can be characterised in that the vibration body comprises two differently-sized cross-sectional surfaces perpendicular to the linear motion direction of the vibration body, that fit the cross-sectional surfaces of he front region of the internal space and of the rear region of the internal space, and in that the cross-sectional surface on the side of the vibration body facing the rear side are at least 100% larger than the cross-sectional surface of the opposite front side of the vibration body, preferably the cross-sectional surface on the side of the vibration body facing the rear side is at least four times the size of the cross-sectional surface of the opposite front side of the vibration body.

The invention also proposes the front region of the internal space to be connected to the rear region of the internal space by means of a transition part. In this context, the invention can preferably provide the transition part to be a wall of the internal space that is oriented to be perpendicular to the direction of motion of the vibration body.

The compressed gas motor can comprise a valve element for regulation of the compressed gas flow into the compressed gas motor, in particular through the gas inlet opening of the compressed gas motor. Said valve element is preferred to be operable by hand.

Accordingly, the invention can further provide the compressed gas motor, except for the vibration body and the restoring element, to be fabricated from thermoplastic materials, whereby polypropylene, polyethylene, polyamide-6, and polyamide-12 are particularly preferred. In addition, all common plastic materials in this technology are well-suited.

Compressed gas motors according to the invention preferably work at a frequency of 500 to 2,000 cycles per minute, particularly preferably at a frequency of 1,000 to 1,500 cycles per minute.

To render the motion of the plunger of the compressed gas motor mechanically usable, the plunger, in particular the side facing away from the vibration body, can have a plunger rod connected to the plunger in mobile manner or a rod connected to the plunger in fixed manner. Preferably, the rod or plunger rod can extend through the compression spring between the plunger and the front side of the internal space and into an opening in the front side of the internal space.

The objects of the invention with regard to a lavage system are met by a lavage system comprising at least one compressed gas motor according to the invention, in which the compressed gas motor or compressed gas motors can be used to generate a periodical spray puff of a liquid.

The objects of the invention are also met by the use of a compressed gas motor according to the invention as motor for a lavage system, a rapping motor, a vibration motor, as drive for a dosing device, as shaker motor or as pump, in particular as lubricant pump.

The underlying objects of the invention are also met by a method for generating a periodical motion by means of a compressed gas, in particular involving the use of a compressed gas motor according to the invention, in which a vibration body of a compressed gas motor is made to vibrate by guiding a compressed gas through the compressed gas motor, whereby the vibration body repeatedly hits against the plunger during the vibration and moves same against a restoring element and the restoring element repeatedly transfers the plunger into a position, in which the vibration body hits the plunger during its vibration, and whereby the motion of the plunger is utilised to drive the compressed gas motor, in particular to generate a spray puff of a liquid.

The underlying objects of the invention are also met by a method for generating a periodical motion by means of a compressed gas, in particular through the use of a compressed gas motor according to the invention, comprising the steps of:

A) in a first position of a vibration body in an internal space, a rear region of the internal space between the vibration body and a rear side of the internal space is connected by a first channel in the vibration body to a gas inlet opening, and a compressed gas is supplied through a gas inlet opening and the first channel into the rear region of the internal space between the vibration body and the rear side of the internal space;

B) the higher pressure in the rear region of the internal space between the vibration body and the rear side of the internal space and the lower pressure being applied on the opposite side of the vibration body accelerate the vibration body in the direction of a front side of the internal space;

C) the motion of the vibration body in the direction of the front side of the internal space separates the connection of the rear region of the internal space between the vibration body and the rear side of the internal space to the gas inlet opening;

D) the motion in the direction of the front side of the internal space makes the vibration body, by a front part of the vibration body, hit against a plunger in a front region of the internal space and accelerates it in the direction of the front side of the internal space, whereby a restoring element takes up and stores energy due to the deflection of the plunger;

E) the motion of the vibration body in the direction of the front side of the internal space connects the rear region of the internal space between the vibration body and the rear side of the internal space by means of the first channel or a second channel in the vibration body to a gas outlet opening;

F) the gas flows from the rear region of the internal space between the vibration body and the rear side of the internal space through the first channel or the second channel and through the gas outlet opening, preferably the gas is dispensed to the surroundings;

G) the plunger is accelerated in the direction of the rear side of the internal space by the release of the energy of the restoring element;

H) the vibration body is accelerated in the direction of the rear side of the internal space by the impact of the plunger and/or by a gas spring and/or a second restoring element;

I) the reverse motion of the vibration body in the direction of the rear side of the internal space separates the connection of the rear region of the internal space between the vibration body and the rear side of the internal space to the gas outlet opening; and J) the reverse motion of the vibration body in the direction of the rear side of the internal space connects the rear region of the internal space between the vibration body and the rear side of the internal space by means of the first channel to the gas inlet opening and the vibration body is transferred into the first position.

The steps preferably proceed in logical and/or chronological order, whereby the periods of time, at which the steps according to the invention proceed, can overlap in part and in time.

Methods according to the invention can provide the cycle to repeat upon a renewed supply of the compressed gas situated into the rear region of the internal space between the vibration body and the rear side of the internal space.

The invention can further provide the part of the rear region of the internal space, which faces the front side of the internal space and is closed, by the rear part of the vibration body, on the side of said part of the internal space facing the rear side, is used as gas spring to accelerate the vibration body in the direction of the rear side of the internal space.

Moreover, methods according to the invention can provide the periodical linear motion of the vibration body in the compressed gas motor to be triggered independently, by the effect of compressed gas without any action of external valves.

Methods according to the invention are preferably repeated at a frequency of 500 to 2,000 cycles per minute, particularly preferably are repeated at a frequency of 1,000 to 1,500 cycles per minute.

The underlying objects of the invention are also met by a method for generating a spray puff comprising the aforementioned process steps according to the invention, whereby, upon a motion of the plunger away from the rear side of the internal space, a rinsing liquid or a liquid-gas mixture is extruded from the front region of the internal space between the plunger and the front side of the internal space through a liquid outlet opening on the front side of the internal space, and, upon a motion of the plunger towards the rear side of the internal space, a liquid or a liquid-gas mixture is pushed or drawn through a liquid inlet opening into the front region of the internal space between the plunger and the front side of the internal space.

In this method, the invention can provide, upon the motion of the plunger towards the front side of the internal space, the pressure in the front region of the internal space between the plunger and the front side of the internal space to open and/or keep open a valve on the liquid outlet opening and to close and/or keep closed a valve connected to the liquid inlet opening, and, upon the motion of the plunger towards the rear side of the internal space, the lower pressure in the front region of the internal space between the plunger and the front side of the internal space to close and/or keep closed the valve on the liquid outlet opening and to open and/or keep open the valve connected to the liquid inlet opening.

The invention is based on the surprising finding that the design according to the invention makes it feasible to have the vibration body periodically hit against the plunger and thus to enable a stably running periodical motion of the plunger at high frequency. The design in this context is very easy and inexpensive to implement and is insensitive to failure. In this context, compressed gas-driven vibrators are preferably based on a compressed gas-induced vibration of the vibration body against a gas cushion and/or a second restoring element.

One important advantage of the compressed gas motor according to the invention as compared to conventional compressed gas motors is that the vibration of the plunger intended to perform the work, and in particular the frequency of the vibration of the plunger, is/are independent of the vibration of the vibration body on which the compressed gas performs the work. As a result, the plunger can run at a different frequency, in particular a higher frequency, than the vibration body. As a result, a significantly higher pumping frequency (two-fold, three-fold, four- or more-fold) can be attained in lavage systems as compared to when the pumping power is driven by the vibration body directly. This obviously applies equally well to other periodical drives, i.e. to applications of the compressed gas motor other than pumps. In this kind of use, no gearing for changing the working frequency of the plunger is required. In return, the force of each individual vibration suffers and the accuracy of the working frequency suffers as well depending on the diligence in building the compressed gas motor. However, this option can be utilised in applications in which this is not overly important.

The invention is based on the rationale to let a compressed gas-driven vibration body that vibrates freely in axial direction act on a plunger that is also mobile in axial direction and is connected to a restoring element, such as a spring element that can be deformed in axial direction. The plunger and the restoring element, or the spring as the case may be, together form a second system capable of vibrating. Said system is made to vibrate upon contact to the vibration body. The vibration body hits against the plunger to transfer momentum, whereby the plunger moves against the restoring element. In this context, the elastic spring element is deformed elastically and/or the restoring element takes up energy. Subsequently, the spring element expands and pushes the plunger back into the starting position. The plunger and the spring element together form a system that vibrates in axial direction.

The compressed gas motor can utilise the compressed gas sources that are present anyway in many areas, in particular in surgical theatres, to drive the compressed gas motor and/or the vibration body. No additional energy source is then needed to drive the compressed gas motor. Simultaneously, the compressed gas is available in virtually unlimited quantity in this setting. Alternatively, the compressed gas motor can just as well be operated with compressed gas cartridges, such as, for example, $CO_2$ cartridges.

Using the lavage system or rinsing system according to the invention, it is feasible to generate pulsed liquid jets at a pulse rate of 1,000 to 2,500 pulses per minute.

A medical rinsing system (lavage system) according to the invention can be composed, for example, of
a) a first hollow cylinder (rear region of the internal space) having a gas inlet opening;
b) a second hollow cylinder (front region of the internal space) having a gas outlet opening, a liquid inlet opening, and a liquid outlet opening, whereby the second hollow cylinder has a smaller internal diameter than the first hollow cylinder;
c) a transition part connecting the first hollow cylinder to the second hollow cylinder;
d) a vibration body with a density of more than 4 $g/cm^3$ that consists of a first cylindrical part (rear part of the vibration body) that is arranged in the first hollow cylinder such as to be mobile ni axial direction, and a second cylindrical part (front part of the vibration body) that is arranged in the second hollow cylinder such as to be mobile in axial direction, whereby the external diameter of the first part of the vibration body is smaller than the internal diameter of the first hollow cylinder and the external diameter of the second part of the vibration body is smaller than the internal diameter of the second hollow cylinder;
e) a plunger that is arranged in the second hollow cylinder such as to be mobile in axial direction;
f) a spring element that is arranged between the narrow side of the second hollow cylinder and the plunger that is mobile in axial direction;
g) a compressed gas supply line;
h) a valve element for regulation of the compressed gas flow;
i) a liquid supply line that is connected to the liquid inlet opening;
j) a liquid dispensing tube that is connected to the liquid outlet opening, and whereby the distance between the plunger, at maximal expansion of the spring element, and the vibration body, at maximal deflection of the vibration body in the direction of the plunger, is such that the vibration body touches the plunger and makes the plunger vibrate in axial direction without the vibration body being stopped.

Lavage systems according to the invention and/or compressed gas motors according to the invention for ejection of a liquid can be provided such that the front side of the plunger opposite from the vibration body and the second hollow cylinder jointly form a pump. For this purpose, a liquid inlet opening and a liquid outlet opening are arranged in the second hollow cylinder. The liquid inlet opening is connected to a valve with a directional effect, for example to a lip valve. This means that the valve only opens if the liquid flows in the direction of the hollow cylinder. A valve with a directional effect is also used on the liquid outlet opening, but opens in reverse if the liquid flow exits from the second hollow cylinder. The space formed by the second hollow cylinder and the front side of the plunger contains the spring element that is supported against the front side of the hollow cylinder (front side of the internal space). Concurrent with an axial vibration of the plunger, the volume of the hollow space formed by the hollow cylinder and the front surface of the plunger increases and decreases periodically. As a result, a positive pressure and a negative pressure are generated periodically. In the presence of negative pressure, liquid is aspirated through the liquid inlet opening, and in the presence of positive pressure, the liquid is extruded from the hollow space through the liquid outlet opening.

A sterile filter can be arranged upstream of the gas inlet opening of the compressed gas motor to filter non-sterile compressed gas, if any is used, in order to prevent microbial contamination of the surgical field. It is feasible just as well to arrange a sterile filter downstream from the gas outlet opening for sterile filtration of the at least partially expanded compressed gas.

It is important to the present invention to have the plunger arranged appropriately such that the vibration body can transfer momentum to the plunger during its axial vibration without the vibration body coming to a standstill. It has been evident that the plunger can be deflected by maximally 3 mm without the vibration body coming to a standstill. The invention can therefore provide the vibration body to shift the plunger by maximally 3 mm in the direction of the front side of the internal space and/or in the direction of the spring.

It has also been evident in the scope of the present invention that rubber-elastic sealing rings for sealing the space between the inside of the front region of the internal space and the external diameter of the plunger are unsuitable, because these permit only low pulse rates due to their friction on the inside of the front region of the internal space. It is therefore preferable to arrange a wiper lip to seal the space between the inside of the front region of the internal space and the external diameter of the plunger. Said wiper lip exerts a lower frictional resistance than common sealing rings. As a result, pulse rates in excess of 1,000 pulses per minute are feasible.

It is also important to the present invention that the vibration body has a density, preferably, of more than 4 g/cm$^3$ and particularly preferably of more than 7 g/cm$^3$. The high density of the vibration body is required in order to be able to transfer a large momentum to the plunger. The vibration body can be fabricated from high-density plastic material, for example heavy spar- or tungsten-filled plastic material, or, just as well, from steel or brass or other metal alloys.

The vibration body preferably possesses at least one gas-permeable channel that extends from the longitudinal side opposite from the plunger in the direction of the plunger, whereby at least two gas-permeable channels are connected to the longitudinal channel and the jacket surface of the vibration body and whereby said channels are arranged at an offset along the longitudinal axis of the vibration body.

BRIEF DESCRIPTION OF THE DRAWINGS

Further exemplary embodiments of the invention shall be illustrated in the following on the basis of six schematic figures, though without limiting the scope of the invention. In the figures:

Identical or similar components are identified in the figures, to some extent, through the same reference numbers even if different compressed gas motors are concerned.

FIGS. 1 to 4 show schematic cross-sectional views of a compressed gas motor 1 according to the invention in chronological order during a working cycle. The cross-sections contain the symmetry axis of the components of the compressed gas motor 1, i.e. the cross-section cuts through the middle. The compressed gas motor 1 comprises a housing 2, 3, 4, 5, 6 made of plastic material and having a two-part cylindrical internal space 7, 8. The housing 2, 3, 4, 5, 6 and/or the internal space 7, 8 is closed on the front side 5 by a cover plate 5 and on the rear side 6 by a rear plate 6.

Figure 1:
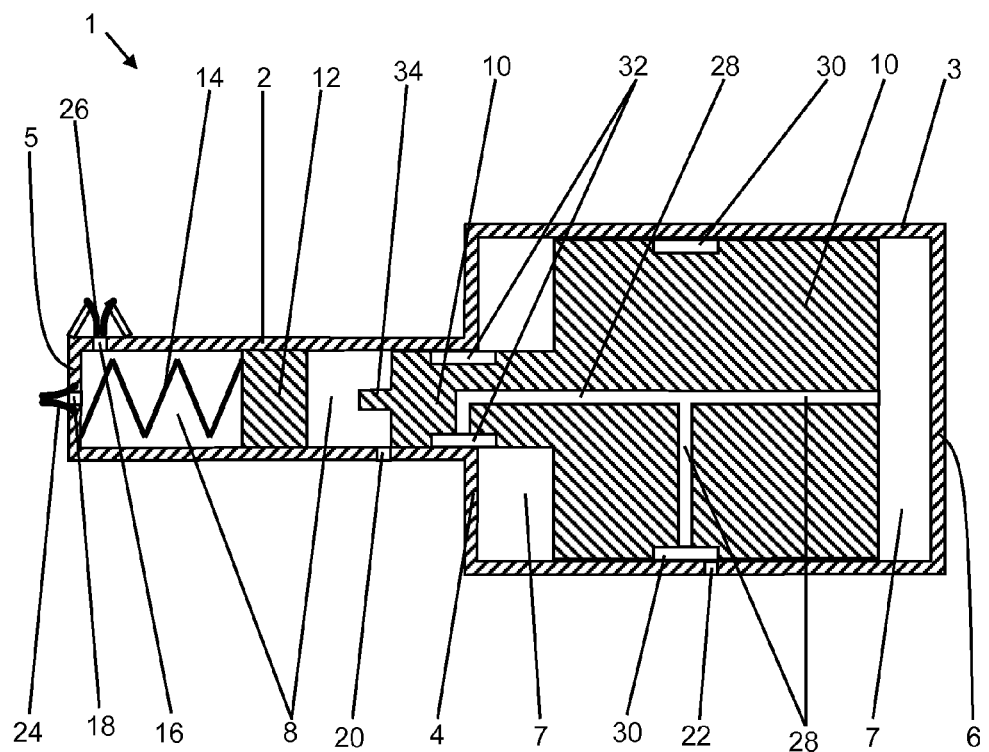
FIG. 1: shows a schematic cross-sectional view of a compressed gas motor according to the invention having a vibration body, in which the gas inlet opening is open and connected to the rear side of the internal space.

The cover plate 5 and the rear plate 6 are both circular discs. The front region 8 of the cylindrical internal space is bordered at the jacket surface by the front wall 2 that is made of a cylindrical tube. The rear region 7 of the cylindrical internal space is bordered at the jacket surface by the rear wall 3 that is also made of a cylindrical tube. The rear region 7 of the internal space has a diameter that is approximately three times larger than that of the front region 8 of the internal space. The transition from the front region 8 of the internal space to the rear region 7 of the internal space is formed by a transition wall 4 that connects the front wall 2 to the rear wall 3 and is arranged parallel to the cover plate 5 and the rear plate 6 and/or parallel to the front side 5 and the rear side 6 of the cylindrical internal space 7, 8. The transition wall 4 is designed to be a circular disc with a central circular recess. The central circular recess and/or the plane of the transition wall 4 forms the boundary between the front region 8 of the internal space and the rear region 7 of the internal space. The central circular recess and the front region 8 of the internal space have the same diameter.

A vibration body 10 is arranged on the inside of the internal space 7, 8. The vibration body 10 is fabricated from brass and takes the shape of two cylinders placed against each other along the symmetry axes by means of their base surfaces. The vibration body 10 is arranged in the internal space 7, 8 such as to be shiftable in linear direction along its cylinder symmetry axis in the direction of the front side 5 and the rear side 6 of the internal space 7, 8. The front part of the vibration body 10 facing the front side 5 fits by its external circumference into the internal circumference of the front region 8 of the internal space. Likewise, the rear part of the vibration body 10 facing the rear side 6 fits by its external circumference into the internal circumference of the rear region 7 of the internal space. Accordingly, the front part of the vibration body 10 can also move in the front region 8 of the internal space.

A plunger 12 made of a firm and mechanically resistant plastic material is arranged between the front side 5 and the vibration body 10 in the front region 8 of the internal space and is used as pump plunger 12 in the compressed gas motor 1 shown here. The plunger 12 is cylindrical in shape such that the jacket surface of the plunger 12 touches against the internal wall of the housing 2. The plunger 12 is supported as in a bearing by means of a compression spring 14 made of steel or a plastic material of suitable elasticity in the front region 8 of the internal space such as to be capable of vibrating. For this purpose, the compression spring 14 is arranged in the front region 8 of the internal space between the plunger 12 and the front side 5 and touches against the plunger 12 and the front side 5.

A liquid inlet opening 16 is provided in the housing wall 2 of the cylinder jacket of the front region 8 of the internal space. The liquid inlet opening 16 is positioned appropriately such that the plunger 12 cannot be arranged between the liquid inlet opening 16 and the front side 5 of the internal space in any of its positions in operation of the compressed gas motor 1. This is to ensure that no liquid can enter into the gap 8 between the plunger 12 and the vibration body 10. To allow the pumping space 8 between the plunger 12 and the front side 5 to be filled with liquid as easily and completely as possible, the liquid inlet opening 16 is arranged as closely as possible to the front side 5 of the internal space 8. The liquid inlet opening 16 can just as well be arranged in the front side 5.

A liquid outlet opening 18 for expelling a jet of liquid is provided in the front side 5. Accordingly, the compressed gas motor 1 is well-suited and designed for generating a pulsed jet of a rinsing liquid from the liquid outlet opening 18.

The side wall 2 of the front region 8 of the internal space has a gas outlet opening 20 provided in it through which the compressed gas supplied into the compressed gas motor 1 and the expanded compressed gas in the compressed gas motor 1 can escape. For this purpose, the gas outlet opening 20 is arranged between the plunger 12, in its maximal deflection in the direction of the rear side 6 and/or in the direction of the vibration body 10, and the plane of the transition wall 4. This is to ensure that the gas outlet opening 20 is covered by the vibration body 10 or is arranged between the vibration body 10 and the plunger 12, and then connects the front region 8 of the internal space, situated in between, to the surroundings.

A gas inlet opening 22 through which the compressed gas is supplied into the compressed gas motor 1 is provided in the cylinder jacket surface of the rear region 7 of the internal space.

The diameter of the rear region 7 of the internal space perpendicular to the cylinder axis is approximately three-fold larger as the diameter of the front region 8 of the internal space, and thus the cross-sectional surface area is approximately nine-fold larger than the cross-sectional surface area of the front region 8 of the internal space. As a result, the rear internal space 7 comprises a front wall 4 (the transition wall 4) in the front and the rear wall 6 in the rear (on the rear side) that connect the walls 3 of the rear internal space to the walls 2 of the front internal space 8. The rear part of the vibration body 10 can be situated at a distance from the transition wall 4 of the rear internal space 7 by means of multiple spacers (not shown), which ensure that the vibration body 10 cannot touch against the transition wall 4 of the rear internal space 7. Since the gas in the gap 7 between the rear part of the vibration body 10 and the transition wall 4 cannot escape at all or not very quickly and therefore is being compressed upon a motion of the vibration body 10 towards the transition wall 4, said gap 7 acts as a gas suspension. Spacers are therefore not really required.

A lip valve 24 is arranged upstream of the liquid outlet opening 18 and is used to close the liquid outlet opening 18, when the pressure in the front region 8 of the internal space between the front side 5 and the plunger 12 is low. The lip valve 24 opens when a liquid is ejected from the front internal space 8, i.e. when the pressure in the front region 8 of the internal space between the plunger 12 and the front side 5 is sufficient. This means that the pressure in the front region 8 of the internal space is higher than the ambient pressure and the elastic force of the lip valve 24.

A lip valve 26 is also arranged upstream of the liquid inlet opening 16 such that liquid can be aspirated into the front region 8 of the internal space only if the pressure in the front region 8 of the internal space is sufficiently low. This is achieved when the plunger 12 moves in the direction of the vibration body 10 and thus the lip valve 24 upstream of the liquid outlet opening 18 is closed. When the lip valve 26 opens, in operation of the compressed gas motor 1 as pumping facility, a liquid flows through the liquid inlet opening 16 into the front region 8 of the internal space.

The rear-side wall 6 closes the rear-side, i.e. the rear, region 7 of the internal space between the vibration body 10 and the rear side 6 in gas-tight and pressure-tight manner. Said rear-side space 7 can be called working space 7.

A channel 28 in the form of a tee is provided in the vibration body 10. Moreover, one circumferential groove 30, 32 each is provided in the lateral cylinder jackets of the two cylindrical parts of the vibration body 10. The tee exits into the rear-side base surface of the vibration body 10 and into the two grooves 30, 32. The channel 28 can comprise a central bore hole along the cylinder axis of the vibration body 10 and multiple or a multitude of radial bore holes connecting the central bore hole to the grooves 30, 32 in the cylinder jacket of the two cylindrical parts of the vibration body 10. The purpose of the circumferential groove 30 in the cylinder jacket with the larger diameter, i.e. in the rear part of the vibration body 10, is to connect the channel 28 to the gas inlet opening 22. The purpose of the circumferential groove 32 in the cylinder jacket with the smaller diameter, i.e. in the front part of the vibration body 10, is to connect the channel 28 to the gas outlet opening 20. The circumferential grooves 30, 32 ensure that the gas inlet opening 22 and the gas outlet opening 20 can be connected to the channel 28 independent of a rotation of the vibration body 10 about its symmetry axis. The channel 28 does not extend to the front side of the vibration body 10.

A projection 34 is arranged on the front side of the vibration body 10 and is provided for the plunger 12 to hit against it. This is to prevent the gas in the front region 8 of the internal space enclosed between the plunger 12 and the vibration body 10 from pushing the plunger 12 prematurely in the direction of the front side 5 and thus from preventing the vibration body 10 from hitting the plunger 12 and thus preventing transfer of a strong momentum. The projection 34 can just as well be arranged on the rear side of the plunger 12.

The gas inlet opening 22 and the gas outlet opening 20 and the grooves 30, 32 and the channel 28 jointly form the valves of the compressed gas motor 1 in the vibration body 10, which can be moved against the openings 20, 22, whereby said valves are automatically controlled by the motion of the vibration body 10. The compressed gas is supplied in the rear region 7 of the internal space between the vibration body 10 and the rear side through the channel 28 of the vibration body 10. The situation is shown in FIG. 1. The compressed gas expands in this region, drives the vibration body 10 in the direction of the plunger 12, and thus performs the work.

The gas inlet opening 22 is being separated from the channel 28 by the motion of the control plunger 10. Moreover, the connection between the channel 26 and/or the front groove 32 and the rear region 7 of the internal space between the vibration body 10 and the transition wall 4 is being separated and said region 7 is thus being closed. The compressed gas in the rear region 7 of the internal space between the vibration body 10 and the rear side 6 continues to expand. Concurrently, the gas in the rear region 7 of the internal space between the vibration body 10 and the transition wall 4 is being compressed and takes up energy.

Figure 2:
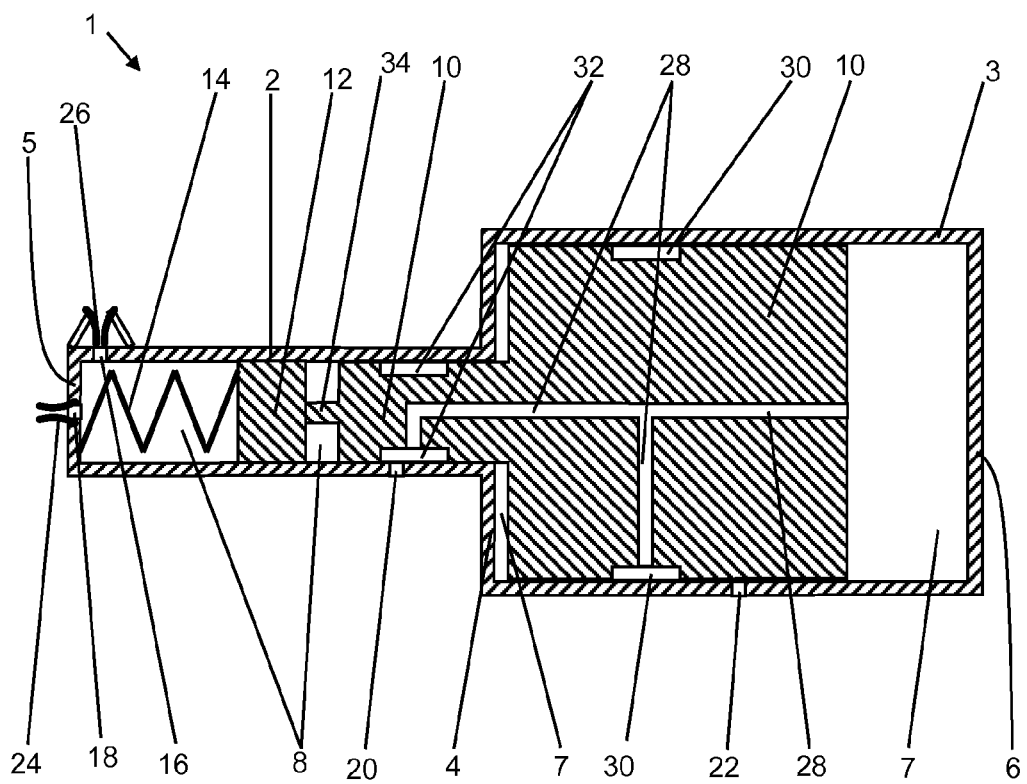
FIG. 2: shows a schematic cross-sectional view of the compressed gas motor according to the invention according to FIG. 1, in which the vibration body is made by the compressed gas or the pressure difference to hit against the plunger and the gas outlet opening is connected to the rear side of the internal space.

Subsequently, the vibration body 10 hits against the plunger 12 and transfers its momentum via the projection 34 to the plunger 12. This situation is shown in FIG. 2.

The transfer of momentum from the vibration body 10 to the plunger 12 accelerates the plunger 12 in the direction of the front side 5 and the compression spring 14 is compressed in the process. Concurrently, the content of the front region 8 of the internal space between the plunger 12 and the front side 5 is ejected through the liquid outlet opening 18 and the lip valve 24. Due to the pressure exerted by the plunger 12 on the content of the front region 8 of the internal space between the plunger 12 and the front side 5, the lip valve 24 stays closed. This prevents the content from being pushed backwards through the liquid inlet opening 16 into the liquid supply.

Due to the transfer of momentum and due to the gas suspension, i.e. the strong reduction in the size of the rear region 7 of the internal space between the vibration body 10 and the transition wall 4, the vibration body 10 is accelerated in the direction of the rear side 6 of the internal space 7, 8. Since the part of the rear region 7 of the internal space facing the rear side 6 is connected to the gas outlet opening 20 by means of the channel 28, the pressure in this region is reduced and the expanded compressed gas is released through the gas outlet opening 20 into the surroundings. The vibration body 10 moves in the direction of the rear side 6 of the internal space 7, 8. As a result, the connection of the channel 28 to the gas outlet opening 20 is being separated again.

Figure 3:
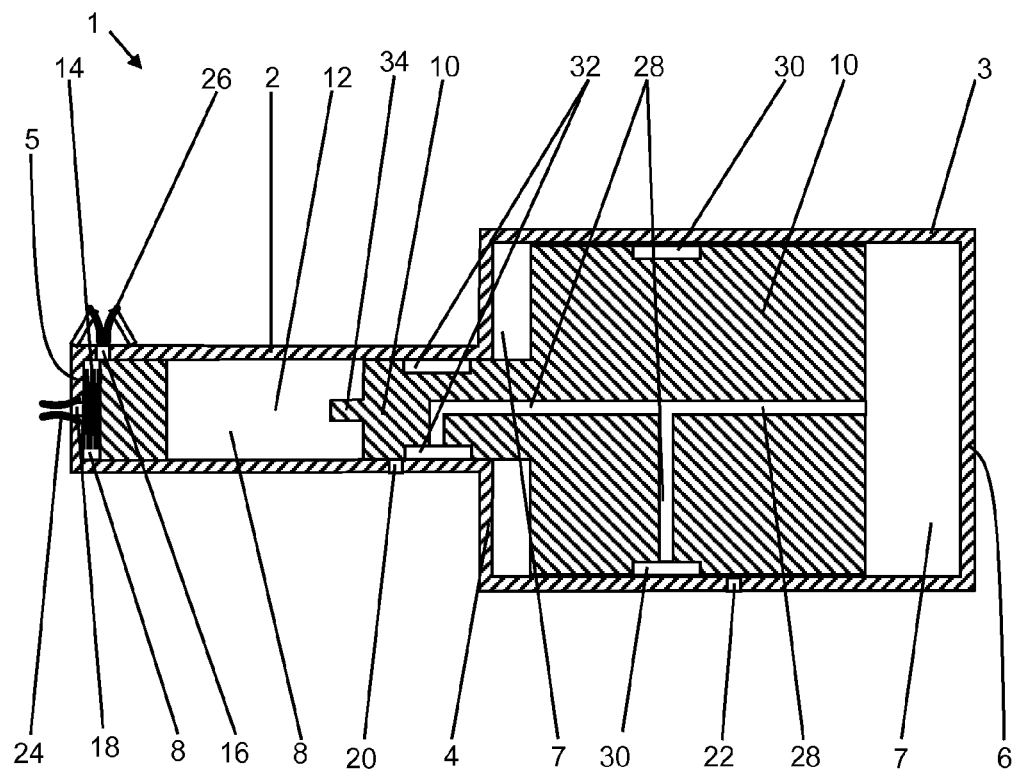
FIG. 3: shows a schematic cross-sectional view of the compressed gas motor according to the invention according to FIG. 1, in which the plunger is moved to the front side and the vibration body resides in a position, in which the gas inlet opening and the gas outlet opening are closed.
Figure 4:
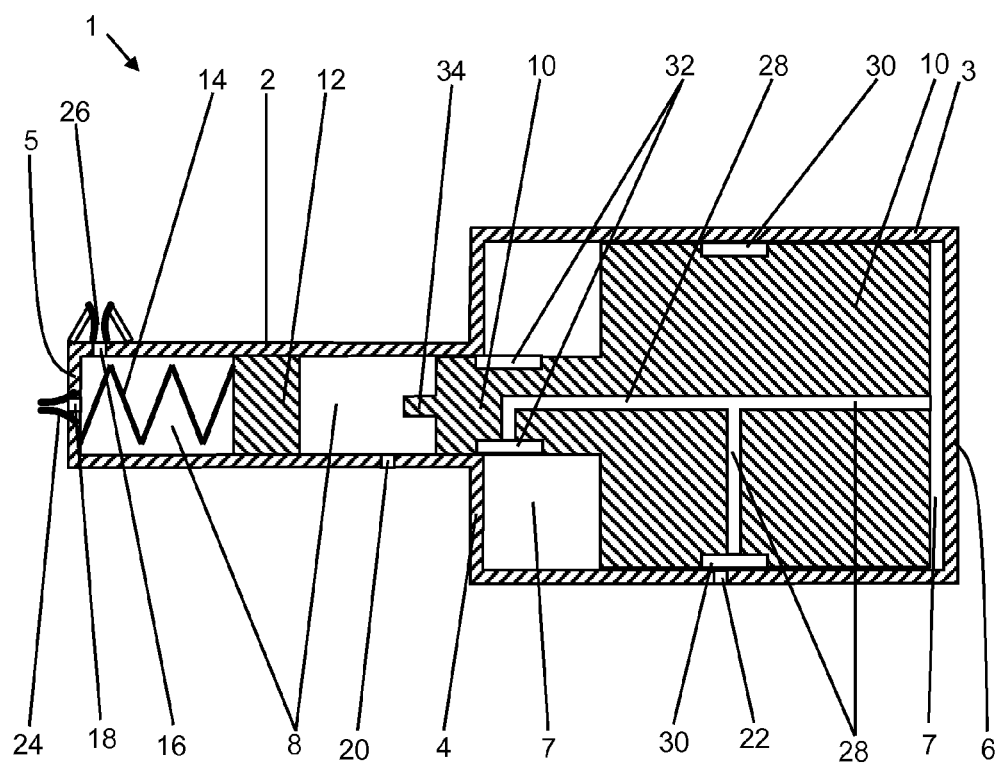
FIG. 4: shows a schematic cross-sectional view of the compressed gas motor according to the invention according to FIG. 1, in which the vibration body almost touches against the rear side of the internal space and compressed gas flows into the rear region of the internal space.

Due to the compression spring 14 being compressed, the plunger 12 is accelerated back in the direction of the vibration body 10. Finally, the plunger 12 reaches the reversal point and the plunger 12 moves back in the direction of the vibration body 10. This situation is shown in FIG. 3.

Due to the gas suspension and its inertia, the vibration body 10 with the rear groove 30 again travels over the gas outlet opening 22 such that the compressed gas again flows through the channel 28 into the rear region 7 of the internal space between the vibration body 10 and the rear side 6. Concurrently, the gas also flows into the rear region 7 of the internal space between the vibration body 10 and the transition wall 4. This is advantageous in that gas losses in the gas suspension formed in the latter region are balanced out during each cycle such that the design does not need to be sealed particularly well in this region. Since the surface area of the vibration body 10 onto which the gas pressure is applied in the part of the rear region 7 of the internal space facing the transition wall 4 is smaller than the part of the rear region 7 of the internal space facing the rear side 6, a pressure difference arises between the two sides of the vibration body 10 and accelerates the vibration body 10 in the direction of the plunger 12. The pressure difference is also explained by the positive pressure of the compressed gas not being applied to the front side of the vibration body 10 in the front region 8 of the internal space, but rather the ambient pressure by means of the gas outlet opening 20, which leads to said pressure difference by means of the difference in surface area between front and rear side of the vibration body 10.

Concurrently, the plunger 12 moves in the direction of the vibration body 10. During this process, the space of the front region 8 between the plunger 12 and the front side 5 increases. The negative pressure thus arising then closes the lip valve 24 on the liquid outlet opening 18 and opens the lip valve 26 on the liquid inlet opening 16. As a result, said space again fills with liquid (not shown) or a liquid-gas mixture.

When the vibration body 10 again moves in the direction of the plunger 12 (FIG. 1), the working cycle of the compressed gas motor 1 starts again.

It is not necessary that the vibration of the plunger 12 and the vibration of the vibration body 10 take place synchronously. It is sufficient to have the vibration body 10 continue to hit against the plunger 12 inducing the plunger to vibrate. Accordingly, the frequency of the system of plunger 12 and spring 14 can be higher than the frequency of the vibrating vibration body 10. The compression spring 14 can be attached to the front side 5 of the internal space 8 and to the plunger 12 for this purpose. The compression spring 14 then also acts on the plunger 12 as a tension spring during the vibration of the plunger 12, By this means, the plunger 12 can attain a significantly higher frequency than is possible for the vibration body 10 or a conventional compressed gas motor.

The invention can provide, for example, that the plunger 12 vibrates at an integral multiple of the frequency of the vibration body 10. The plunger 12 is being hit by the vibration body 10, for example, during every second or third vibration. Frequency deviations are insignificant in this context since the transfer of the momentum of the denser and heavier vibration body 10, in case of doubt, forces its resonant frequency on the vibration of the plunger 12. Accordingly, any rational or irrational relationship between the frequencies of the vibrations can be used to implement the compressed gas motor 1 according to the invention.

If the spring 14 is not attached to the plunger 12 and the front side 5, the plunger 12 hits against the vibration body 10, at some point in time, by its surface facing the rear side 6. Depending on the direction of motion of the vibration body 10 at said point in time, it bounces off the vibration body 10 to a different degree and takes on some momentum in the direction of the front side 5 from the vibration body 10 that drives the vibration of the plunger 12.

Accordingly, even if the compressed gas motor 1 is not designed with diligence, i.e. if the resonant frequencies of the plunger 12 and vibration body 10 are not matched to each other, the compressed gas motor 1 will still work well. As a result, the compressed gas motor 1 can also be operated by compressed gas of different pressure.

Figure 5:
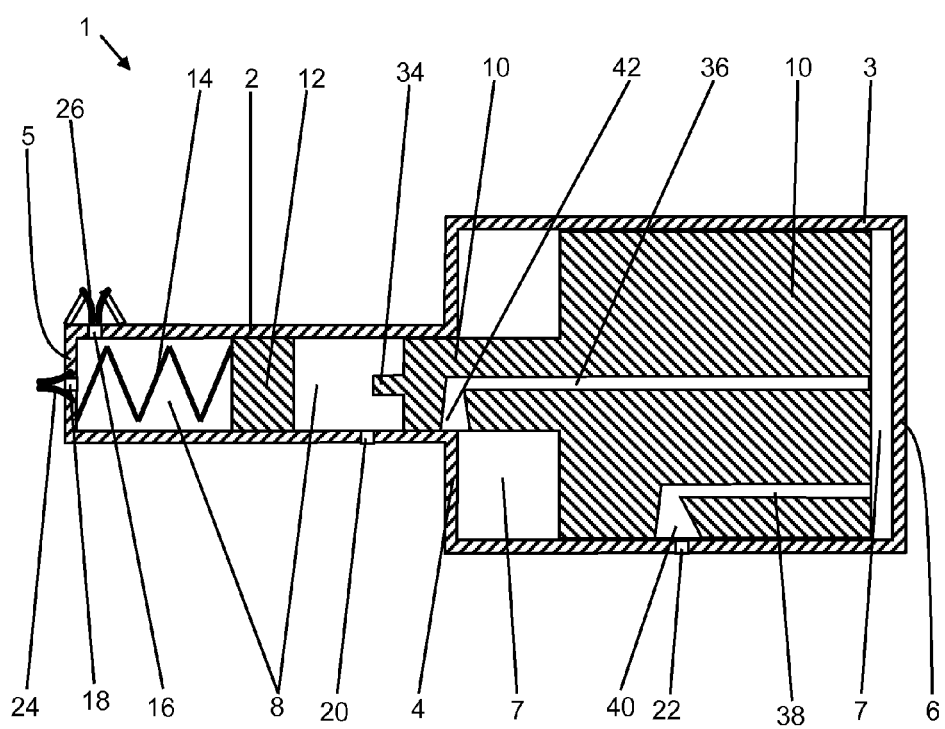
FIG. 5: shows a schematic cross-sectional view of the alternative compressed gas motor according to the invention having two channels.

FIG. 5 shows a schematic cross-sectional view of the alternative compressed gas motor 1 according to the invention. The design of said compressed gas motor 1 resembles the one according to FIGS. 1 to 4 with the exception of the channel 28, the grooves 30, 32, and the symmetry of the internal space 7, 8, of the plunger 12, and of the vibration body 10 (see FIGS. 1 to 4). Instead of a channel shaped as a tee, two channels 36, 38 are provided on the inside of the vibration body 10 according to FIG. 5. The purpose of the first channel 36 is to connect the rear region 7 of the internal space between the vibration body 10 and the closed rear side 6 to the rear region 7 of the internal space between the vibration body 10 and the transition wall 4 or to the gas outlet opening 20. The purpose of the second channel 38 is to connect the rear region 7 of the internal space between the vibration body 10 and the closed rear side 6 to the gas inlet opening 22.

The shapes of the internal space 7, 8, of the vibration body 10 and of the plunger 12 are selected to match each other in this embodiment, but are not rotationally symmetrical. A cylindrical shape with a base surface that is rounded, but is not circularly symmetric, for example with an oval base surface, is preferred. This requires a little more effort in the manufacture. However, the vibration body 10 can be prevented from rotating in the rear region 7 of the internal space by this means. To be exact, it is sufficient to have just the rear region 7 of the internal space and the rear part of the vibration body 10 not be rotationally symmetrical. In this case, the plunger 12 and the front region 8 of the internal space can just as well have a circular-cylindrical symmetry.

Since the vibration body 10 in this refinement can no longer rotate in the internal space 7, 8, lateral bore holes in the jacket surfaces of the vibration body 10 can make sure that the exits 40, 42 of the channels 36, 38 meet the gas inlet opening 22 and the gas outlet opening 20. In order to enable gas exchange over somewhat longer periods of time during a vibration, the exits 40, 42 are broadened in longitudinal direction. But this is not obligatory for the compressed gas motor 1 to work.

The functional principle and the working cycle of the compressed gas motor 1 according to FIG. 5 are the same as those of the compressed gas motor 1 according to FIGS. 1 to 4.

Instead of ejecting a liquid through the liquid outlet opening 18, the compressed gas motors according to FIGS. 1 to 5 can have a rod (not shown) be connected firmly, or have a piston rod (not shown) be connected by means of a joint, to the front side of the plunger 12, which extend forward out of the compressed gas motor 1. For example, the rod or plunger rod can extend out of the compressed gas motor 1 through a central opening similar to the liquid outlet opening 18. The rod or piston rod can be used, for example, as a drive for a flywheel or as a shaking facility.

Figure 6:
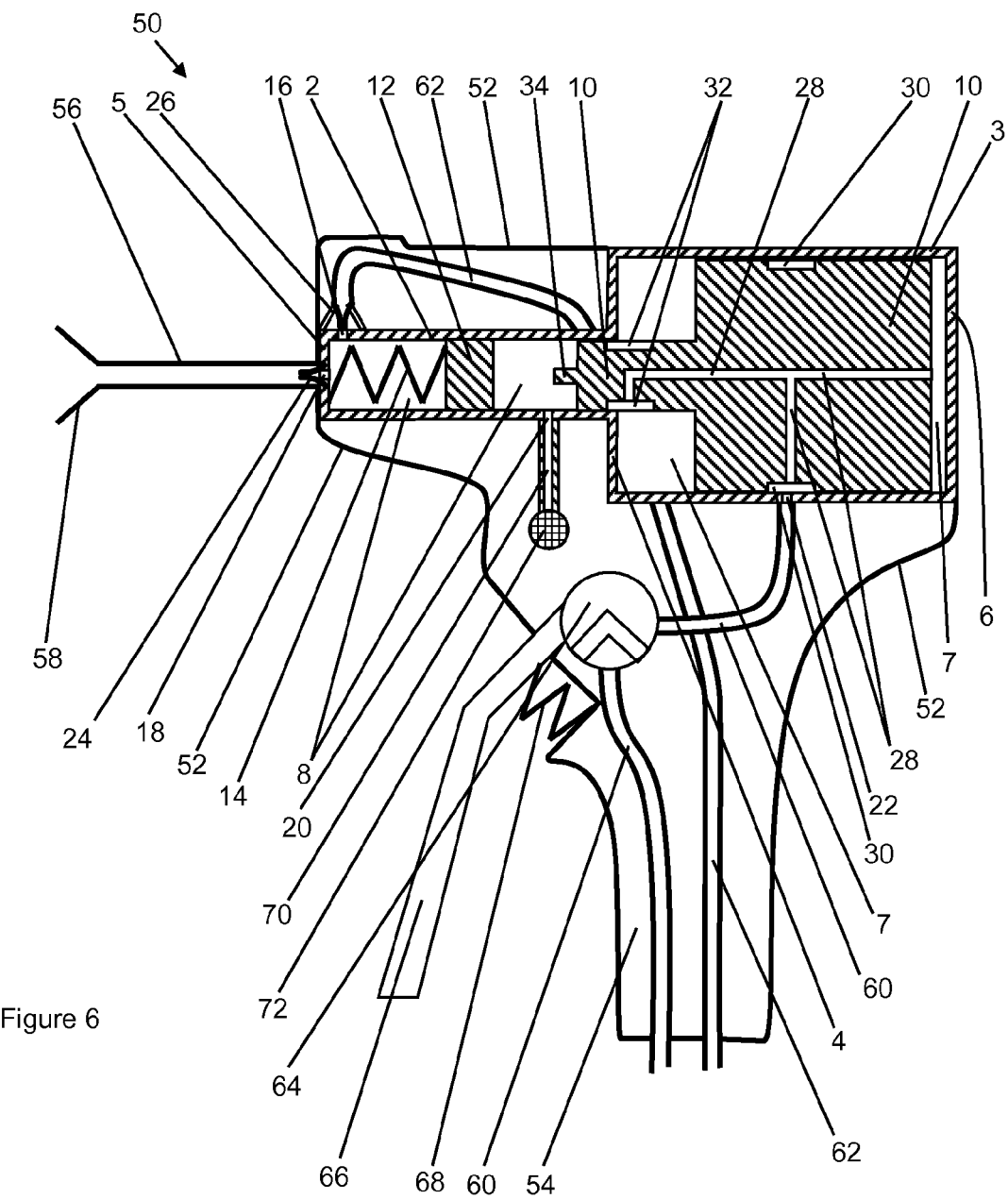
FIG. 6: shows a schematic cross-sectional view of a lavage system according to the invention having a compressed gas motor according to the invention.

FIG. 6 shows a schematic cross-sectional view of a lavage system 50 according to the invention that can be held in one hand and has a compressed gas motor 1 according to the invention of the type shown in FIGS. 1 to 4. Since said compressed gas motor is designed alike the compressed gas motor 1 according to FIGS. 1 to 4, reference shall be made to said exemplary embodiment in terms of said design. Alternatively, it is just as well to incorporate the compressed gas motor 1 according to FIG. 5 or any other compressed gas motor according to the invention.

The lavage system 50 comprises a housing 52 made of plastic material, in which the compressed gas motor is arranged. A pistol grip 54 is formed by the housing 52 and allows the lavage system to be held by one hand. The liquid outlet opening 18 exits via the lip valve 24 into a tube 56, which, in turn, exits in a funnel 58, The pulsed liquid jet is dispensed via the funnel 58.

The gas inlet opening 22 of the compressed gas motor is connected to a compressed gas supply line 60, which, in turn, is connected to a compressed gas source (not shown). The liquid supply opening 16 is connected to a liquid supply line 62 by means of which a medical rinsing liquid is supplied into the compressed gas motor. A manually-operable rotary valve element 64 is arranged in the compressed gas supply line 60 and is operable by means of a trigger 66 using the same hand that is used to hold the lavage system 50 by the pistol grip 54. A compression spring 68 is used to rotate the trigger 66 away from the pistol grip 54 and thus to rotate the rotary valve element 64 into the closed position.

A gas discharge line 70 is arranged on the gas outlet opening 20 and extends laterally towards the outside and connects the gas outlet opening 20 to the surroundings of the lavage system 50. A filter 72 and/or a sterile filter 72 is arranged in the exit to the surroundings or in the gas discharge line 70. This prevents any ingress of interfering particles through the gas discharge line 70 and the gas outlet opening 20 into the compressed gas motor, and preferably prevents contamination of the surgical field as well.

A compressed gas is supplied via the compressed gas supply line 60 to the valve element 64. The valve element 64 can be operated manually by means of the trigger 66 in the way of a pistol. The gas feed line 60 continues downstream from the manually operable control valve 64 and is connected to the gas outlet opening 26 of the compressed gas motor. As a result, the compressed gas motor and/or the lavage system 50 can be controlled by the trigger 66.

As an alternative to the lip valve 26, a non-return valve (not shown) can just as well be arranged in the rinsing liquid supply line 62. The compressed gas supply line 60 and the liquid supply line 62 are guided into the pistol grip 54 on the bottom side.

In lavage systems 50 of this type, it is preferred to provide an aspiration facility (not shown) by means of which excess liquid and parts removed along with the liquid are aspirated and discharged via a separate funnel and a separate tube (not shown). Preferably, an aspiration line connected to the aspiration facility is also guided through the bottom side of the pistol grip 54 for this purpose. The aspiration tube can surround the tube 56 in concentric manner.

When the valve element 64 is operated by means of the trigger 66, the compressed gas supply line 60 becomes through-going and compressed gas is supplied into the compressed gas motor and/or into the rear region 7 of the internal space. The resulting pressure difference between the front side (on the left in FIG. 6) of the vibration body 10 and the rear side (on the right in FIG. 6) of the vibration body 10 makes the vibration body 10 move and the compressed gas motor works as described above with respect to FIGS. 1 to 4. Concurrently, the rinsing liquid conveyed from an external liquid reservoir (not shown) through the liquid supply line 62 periodically flows into the gap 8 between the pump plunger 12 and the front wall 5 of the compressed gas motor 1.

The rinsing liquid is ejected from the compressed gas motor 1 through periodical puffs through the lip valve 24 and the tube 56 and the liquid outlet opening 18 for as long as compressed gas is applied to the gas inlet opening 22 and compressed air or compressed gas flows through the gas inlet opening 22 into and through the compressed gas motor 1. The process is terminated when the control valve 64 is no longer being operated and the gas discharge line 60 is thus interrupted and/or closed. The rotary valve element 64 is restored by means of the elastic spring 68. The plunger 12 is then moved by the spring element 14 in the compressed gas motor, and the plunger 12 and the vibration body 10 are moved by the gas suspension on the front side of the vibration body 10 in the rear region of the internal space 7, into the starting position shown, and the lavage system 50 is immediately ready for use again.

Instead of just one compressed gas motor 1, a lavage system 50 can just as well comprise two or more compressed gas motors 1, whose compressed gas connectors are arranged parallel to each other. This effects a reinforcement of the spray jet thus generated or attains a higher pulse rate, for example a jet of rinsing liquid of doubled frequency.

All embodiments of the compressed gas motors can provide an additional spring element (not shown), such as, for example, another compression spring, for support of or as an alternative to the gas suspension in the rear region 7 of the internal space between the vibration body and the transition wall 4. By means of said additional spring element, the vibration body 10 is pushed in the direction of the rear side 6 of the internal space. Moreover, said second spring element can also be utilised to set the working frequency of the vibration body 10 and thus to fine-tune the compressed gas motor 1.

The features of the invention disclosed in the preceding description and in the claims, figures, and exemplary embodiments, can be essential for the implementation of the various embodiments of the invention both alone and in any combination.

LIST OF REFERENCE NUMBERS

1 Compressed gas motor
2 Housing/lateral wall of the front region of the internal space
3 Housing/lateral wall of the rear region of the internal space
4 Housing/transition wall between the front region and the rear region of the internal space
5 Housing/cover plate and front side of the internal space
6 Housing/rear plate and rear side of the internal space
7 Rear region of the internal space
8 Front region of the internal space
10 Vibration body
12 Plunger
14 Spring element/compression spring
16 Liquid inlet opening
18 Liquid outlet opening
20 Gas outlet opening
22 Gas inlet opening
24 Lip valve
26 Lip valve
28 Channel
30 Circumferential groove
32 Circumferential groove
34 Projection
36 Channel
38 Channel
40 Exit
42 Exit
50 Lavage system
52 Housing
54 Pistol grip
56 Tube
58 Funnel
60 Compressed gas supply line
62 Liquid supply line
64 Valve element/rotary valve element
66 Trigger
68 Spring
70 Gas discharge line
72 Filter

The invention claimed is:

1. A compressed gas motor having a total length defined between a front side and a closed rear side when the compressed gas motor is located in an upright position, the compressed gas motor comprises:
    a vibration body configured to vibrate by a compressed gas being guided through the compressed gas motor; and
    a plunger supported by a restoring element in spring-like manner,
    wherein the vibration body and the plunger are appropriately positioned and supported such that the vibration body repeatedly contacts the plunger during a vibration of the vibration body and displaces the plunger against the restoring element,
    wherein the plunger is movable by the restoring element into a position, in which the vibration body contacts against the plunger during the vibration of the vibration body, such that the vibration body repeatedly contacts the plunger during the vibration of the vibration body,
    wherein the motion of the plunger is configured to be the drive of the compressed gas motor, and
    wherein the plunger has a rear face directly facing the vibration body, the vibration body has a rear face directly facing the closed rear side of the compressed gas motor and a total surface area of the rear face of the plunger directly facing the vibration body is less than a total surface area of the rear face of the vibration body directly facing the closed rear side of the compressed gas motor.

2. The compressed gas motor according to claim 1, wherein the restoring element is configured to exert a force on the plunger acting in a direction of the vibration body, at least for a part of a time during operation of the compressed gas motor.

3. The compressed gas motor according to claim 1, wherein the compressed gas motor further comprises at least a first internal space and a second internal space, wherein the vibration body is arranged in the first internal space and the plunger is arranged in the second internal space to be mobile in a linear direction and in that the first and second internal spaces are bordered by the front side, the closed rear side, and a circumferential side wall connecting the front side and the closed rear side, wherein the plunger is arranged between the front side and the vibration body.

4. The compressed gas motor according to claim 3, wherein the first and second internal spaces comprise a front region having a cross-sectional surface that is smaller than a cross-sectional surface of a rear region, wherein the plunger is arranged in the front region between the front side and the vibration body such as to be mobile in the linear direction.

5. The compressed gas motor according to claim 4, wherein the vibration body comprises a front part having a cross-section matching the cross-sectional surface of the front region such that the front part of the vibration body closes the front region on a side facing a rear side at least for a part of a time during an operation of the compressed gas motor, and wherein the vibration body comprises a rear part having a cross-section matching the cross-sectional surface of the rear region such that the rear part of the vibration body separates the rear region into two parts.

6. The compressed gas motor according to claim 3, wherein a gas inlet opening configured to supply a gas into the first internal space is provided in the side wall in a rear region of the first internal space and in that a gas outlet opening configured to discharge of the gas from the second internal space is provided in the side wall in a front region of the second internal space.

7. The compressed gas motor according to claim 6, wherein the first and second internal spaces between the plunger and a rear side of the first internal space is closed except for the gas inlet opening and the gas outlet opening.

8. The compressed gas motor according to claim 6, wherein at least one channel configured to guide the gas is provided in the vibration body, wherein the at least one channel connects the rear region of the first internal space between the vibration body and the rear side of the first internal space to the gas inlet opening or to the gas outlet opening dependent upon a position of the vibration body in the first internal space.

9. The compressed gas motor according to claim 8, wherein the vibration body, in a first position, connects the rear region of the first internal space between the vibration body and the rear side of the first internal space by means of the at least one channel to the gas inlet opening and separates the at least one channel from the gas outlet opening, and, in a second position, connects the rear region of the second internal space between the vibration body and a rear side of the first internal space by means of the at least one channel to the gas outlet opening and separates the at least one channel from the gas inlet opening.

10. The compressed gas motor according to claim 9, wherein the vibration body, in a third position between the first position and the second position, covers both the gas inlet opening and the gas outlet opening.

11. The compressed gas motor according to claim 8, wherein the at least one channel extends from the side of the vibration body facing the rear side to a lateral jacket surface of a rear part of the vibration body, and the same or any other channel extends from a side of the vibration body facing a rear side to a lateral jacket surface of a front part of the vibration body, wherein the vibration body comprises just one channel configured as a tee and extends from the side of the vibration body facing the rear side to the lateral jacket surface of the rear part of the vibration body and to the lateral jacket surface of the front part of the vibration body.

12. The compressed gas motor according to claim 3, wherein a liquid inlet opening is provided in a front region of the second internal space in the side wall of the second internal space and a gas outlet opening is provided in the front side of the second internal space, a valve is arranged on the liquid inlet opening.

13. The compressed gas motor according to claim 12, wherein the valve is arranged on the liquid inlet opening and opens when a low pressure arises in the front region of the second internal space due to a motion of the plunger away from the front side, and a valve is arranged on a liquid outlet opening that opens when a high pressure arises in the front region of the second internal space due to a motion of the plunger towards the front side.

14. The compressed gas motor according to claim 12, wherein the liquid inlet opening, in operation of the compressed gas motor, is not covered by the plunger at least for a part of a time of the operation of the compressed gas motor, and the liquid inlet opening, in a non-covered state, is arranged between the plunger and the front side of the second internal space.

15. The compressed gas motor according to claim 12, wherein a tube or a hose is connected to the liquid inlet opening and opens when there is a negative pressure in the front region of the second internal space between the plunger and the front side of the second internal space enabling a supply of liquid into the front region of the second internal space.

16. The compressed gas motor according to claim 3, wherein the first and second internal spaces, or at least regions thereof, are cylindrical or is cylindrical in a region of a working space of the vibration body and/or plunger or in an entire swept volume of the plunger and vibration body.

17. The compressed gas motor according to claim 1, wherein the restoring element is an elastic compression spring that is arranged in a front region of the second internal space between the plunger and a front side of the second internal space.

18. The compressed gas motor according to claim 1, wherein the vibration body has a density of at least 4 g/cm$^3$.

19. The compressed gas motor according to claim 1, wherein the restoring element moves the plunger into a position, in which a side of the vibration body facing the plunger, at maximal deflection of the vibration body in a direction of the plunger, contacts against the side of the plunger facing the vibration body to accelerate the plunger in a direction away from the vibration body.

20. A lavage system comprising at least one compressed gas motor according to claim 1, in which the at least one compressed gas motor generates a periodical spray puff of a liquid.

21. A motor for a lavage system, wherein the motor comprises a compressed gas motor according to claim 1, and wherein the compressed gas motor is a rapping motor, a vibration motor, a drive for a dosing facility, a shaker motor or a lubricant pump.

22. A method for generating a periodical motion with a compressed gas, the method comprises:
providing the compressed gas motor according to claim 1, wherein vibrating the vibration body of the compressed gas motor by guiding a compressed gas through the compressed gas motor, wherein the vibration body repeatedly contacts against the plunger during the vibration of the vibration body and moves the plunger against the restoring element and the restoring element repeatedly transfers the plunger into a position, in which the vibration body contacts the plunger during the vibration of the vibration body, and wherein a motion of the plunger drives the compressed gas motor to generate a spray puff of a liquid.

23. A method for generating a periodical motion with a compressed gas, the method comprising:
providing the compressed gas motor according to claim 1, wherein, in a first position of the vibration body in an internal space, a rear region of the internal space between the vibration body and a rear side of the internal space is connected by a first channel in the vibration body to a gas inlet opening, and a compressed gas is supplied through the gas inlet opening and the first channel into the rear region of the internal space between the vibration body and the rear side of the internal space;
accelerating the vibration body in the direction of a front side of the internal space by applying a higher pressure in the rear region of the internal space between the vibration body and the rear side of the internal space and a lower pressure on the opposite side of the vibration body;
separating a connection of the rear region of the internal space between the vibration body and the rear side of the internal space to the gas inlet opening by a motion of the vibration body in the direction of the front side of the internal space, wherein the motion in the direction of the front side of the internal space makes the vibration body, by a front part of the vibration body, contact the plunger in a front region of the internal space and accelerates the plunger in the direction of the front side of the internal space, wherein the restoring element takes up and stores energy due to a deflection of the plunger, wherein the motion of the vibration body in the direction of the front side of the internal space connects the rear region of the internal space between the vibration body and the rear side of the internal space by means of the first channel or a second channel in the vibration body to a gas outlet opening;

flowing the gas from the rear region of the internal space between the vibration body and the rear side of the internal space through the first channel or the second channel and through the gas outlet opening, wherein the gas is dispensed to the surroundings;

accelerating the plunger in the direction of the rear side of the internal space by the release of the energy of the restoring element;

accelerating the vibration body in the direction of the rear side of the internal space by the impact of the plunger and/or by a spring;

separating the connection of the rear region of the internal space between the vibration body and the rear side of the internal space to the gas outlet opening by a reverse motion of the vibration body in the direction of the rear side of the internal space; and connecting, by the reverse motion of the vibration body in the direction of the rear side of the internal space, the rear region of the internal space between the vibration body and the rear side of the internal space by means of the first channel to the gas outlet opening, such that the vibration body is transferred into the first position.

24. The method according to claim 23, wherein a part of the rear region of the internal space, which faces the front side of the internal space and is closed, by a rear part of the vibration body, on a side of the part of the internal space facing the rear side, is used as a gas spring to accelerate the vibration body in the direction of the rear side of the internal space.

25. The method according to claim 23, wherein, upon a motion of the plunger away from the rear side of the internal space, a rinsing liquid or a liquid-gas mixture is extruded from the front region of the internal space between the plunger and the front side of the internal space through a liquid outlet opening on the front side of the internal space and, upon a motion of the plunger towards the rear side of the internal space, a liquid or a liquid-gas mixture is pushed or drawn through a liquid inlet opening into the front region of the internal space between the plunger and the front side of the internal space.

26. The method according to claim 25, wherein, upon the motion of the plunger towards the front side of the internal space, a pressure in the front region of the internal space between the plunger and the front side of the internal space opens and/or keeps open a valve on the liquid outlet opening and closes and/or keeps closed a non-return valve connected to the liquid inlet opening, and, upon the motion of the plunger towards the rear side of the internal space, a lower pressure in the front region of the internal space between a working plunger and the front side of the internal space closes and/or keeps closed the valve on the liquid outlet opening and opens and/or keeps open the non-return valve connected to the liquid inlet opening.

* * * * *